United States Patent [19]

Averbuch et al.

[11] Patent Number: 4,632,922

[45] Date of Patent: Dec. 30, 1986

[54] OXOMORPHOLINYL DIMER AND RESCUE OF ANTHRACYCLINE AND MITOMYCIN C DAMAGE

[75] Inventors: Steven D. Averbuch, Rockville; Nicholas R. Bachur, Towson, both of Md.; Giorgio Gaudiano; Tad H. Koch, both of Boulder, Colo.

[73] Assignees: The United States of America as represented by the Department of Health and Human Services, Washington, D.C.; University of Colorado Foundation, Inc., Colo.

[21] Appl. No.: 791,120

[22] Filed: Oct. 24, 1985

[51] Int. Cl.$^4$ .................. A61K 31/535; C07D 265/32
[52] U.S. Cl. ........................................ 514/236; 544/87

[58] Field of Search ......................... 544/87; 514/236

[56] References Cited

FOREIGN PATENT DOCUMENTS 137971 12/1978 Japan .
464586 3/1975 U.S.S.R. .

Primary Examiner—Robert W. Ramsuer
Attorney, Agent, or Firm—Holman & Stern

[57] ABSTRACT

The present invention discloses a bi(3,5-dimethyl-5-hydroxymethyl-2-oxomorpholin-3-yl) compound and its efficacy as a rescue agent against anthracycline and mitomycin C induced tissue damage. A method of synthesizing said compound has also been described.

2 Claims, 12 Drawing Figures

OXOMORPHOLINYL DIMER AND RESCUE OF ANTHRACYCLINE AND MITOMYCIN C DAMAGE

BACKGROUND OF THE INVENTION

1. Technical Field

The present invention is related to the preparation of an oxomorpholinyl dimer and its efficacy as a rescue agent against anthracycline and mitomycin C induced tissue damage. More particularly, the present invention is related to the synthesis of bi(3,5-dimethyl-5-hydroxymethyl-2-oxomorpholin-3-yl) and its use as a protective drug for the prevention or treatment of anthracycline and mitomycin C induced tissue injury.

2. State of the Art

Anthracycline compounds, particularly doxourubicin and daunorubicin, and mitomycin C are useful drugs in the treatment of human malignant diseases. However, the clinical application of these compounds is limited by their tissue or organ toxicity. For instance, tissue necrosis following drug extravasation is a well recognized complication resulting from the intravenous administration of doxorubicin (DOX) or mitomycin C (MIT). The local toxicity is characterized initially by pain, erythema, and swelling at the site of extravasation. The clinical course of tissue damage is variable and indolent, but it can progress to ulcer formation and necrosis of deep subcutaneous structures including tendons, joints, and nerves. Extensive surgical debridement may be required and infection and/or loss of limb function may be secondary complications of this injury.

Of utmost importance in the prevention of drug-induced skin injury is meticulous intravenous technique. However, even when DOX or MIT is administered by experienced and well-trained chemotherapy personnel, the incidence of extravasation may be high. Newer schedules of drug administration, such as weekly dosing or continuous infusion may increase the chance of drug extravasation.

Recommendations for the local treatment of DOX or MIT extravasation are based largely on anecdotal or uncontrolled clinical studies and many agents have been cited as putative antidotes for drug-induced injury. Several animal models have been developed to test the efficacy of these potential antidotes. However, the skin of most of these species differs considerably from human skin and these models have failed to establish a consistently effective pharmacologic treatment for DOX-induced injury. Recently, a swine model was developed to study DOX skin toxicity (Wolgemuth, et al., Proc. Am. Assoc. Cancer Res. 23:171, 1982; Desai, et al., Cancer Treat. Rep. 66:1371-1374, 1982) and only one report has adequately demonstrated predictable and reproducible lesions following intradermal injections of DOX (Okano, et al., Cancer Treat. Rep. 67:1075-1078, 1983). Again, no clear protection against necrosis, by any of 11 agents tested in this model, could be shown, although dimethyl sulfoxide appeared to ameliorate the severity of injury.

Bi(3,5-dimethyl-5-hydroxymethyl-2-oxomorpholin-3-yl) (DHM3) of the present invention represents a class of radical dimer compounds that reacts with DOX in vitro to produce the insoluble and pharmacologically inactive 7-deoxyaglycone metabolite. Various benefits of DHM3 of the present invention are demonstrated.

SUMMARY OF INVENTION

It is, therefore, an object of the present invention to provide a bi(3,5-dimethyl-5-hydroxymethyl-2-oxomorpholin-3-yl) compound and a method of synthesizing the same.

It is another object of the present invention to provide a method of preventing or treating anthracycline or MIT induced extravasation skin necrosis.

Other objects and advantages would become apparent as the detailed description of the present invention proceeds.

BRIEF DESCRIPTION OF DRAWINGS

These and other objects, features and many of the attendant advantages of the invention will be better understood upon a reading of the following detailed description when considered in connection with the accompanying drawings wherein.

DETAILED DESCRIPTION OF INVENTION

The above objects and advantages of the present invention are achieved by providing a novel class of drug, viz., bi(3,5-dimethyl-5-hydroxymethyl-2-oxomorpholin-3-yl) and a method of synthesizing the same.

Although any similar or equivalent methods and materials can be used in the practice of the present invention or for the tests described herein, the preferred methods and materials are now described. All publications mentioned hereunder are incorporated herein by reference.

Methods and Materials

Infrared spectra were recorded with a Perkin-Elmer model 337 infrared spectrophotometer and $^1$H NMR spectra with a Varian Associates EM390 spectrometer. Chemical shifts are reported in parts per million on the $\delta$ scale from internal Me$_4$Si, unless otherwise specified. EPR spectra were recorded with a Varian Associates E109 spectrometer equipped with field/frequency lock. A Hewlett Packard 8450A rapid-scan spectrometer was used for ultraviolet and visible spectra. Microanalyses were performed by Atlantic Microlab, Atlanta, GA. All solvents were reagent grade or spectroanalyzed and commercially available. Daunorubicin was obtained from the Drug Development Branch of the National Cancer Institute, Bethesda, MD. All analyses were performed following conventional, routine procedures well known in the art, unless otherwise indicated.

Condensation of 2-amino-2-methy-1,3-propanediol with ethyl pyruvate

Figures 1, 2:
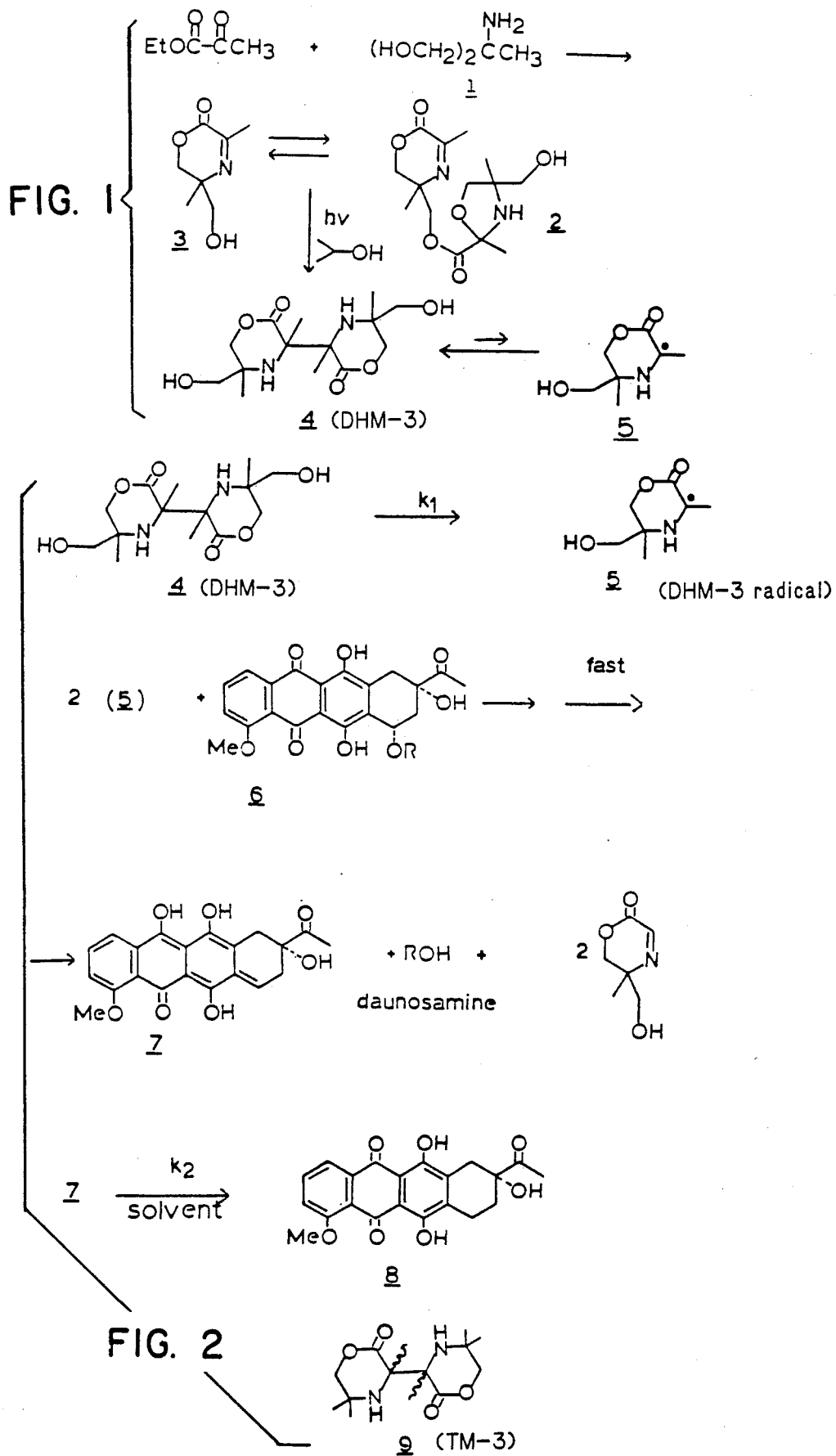
FIG. 1 shows the synthesis of bi(3,5-dimethyl-5-hydroxymethyl-2-oxomorpholin-3-yl) (DHM-3) from 2-amino-2-methyl-1,3-propanediol and ethyl pyruvate.
FIG. 2 shows the proposed mechanism for reductive cleavage of daunorubicin by DHM-3 and the structure of TM-3 (9).

As shown schematically in FIG. 1, 2-Amino-2-methyl-1,3-propanediol (1, 10.5 g, 0.10 mol) from (Aldrich Chemical, Milwaukee, Wis.) and ethyl pyruvate (11.6 g, 0.10 mol) from Sigma Chemical, St. Louis, MO. were dissolved in 200 ml of 1-butanol (Fisher Scientific, Fair Lawn, NJ). The solution was heated to cause the 1-butanol to reflux for 45 min under a nitrogen atmosphere in a flask equipped with a Dean-Stark trap to remove water and ethanol. The distillate (50 ml) was collected in the trap. After cooling to ambient temperature (about 20°–28° C.), the solvent was rotary evaporated, and the residue was vacuum distilled. The product, oxazinone 2, was collected as a viscous colorless oil, b.p. 120°–135° C. at 0.4 Torr. Conventional silica gel thin layer chromatography (TLC), eluting with dichloromethane-methanol (93:7, v/v), gave one spot with Rf=0.5. The UV spectrum in 2-propanol solvent showed a maximum at 323 nm whose extinction coefficient slowly increased from 157 to 188 l/mol.cm in 20 h. The UV spectrum in water showed a maximum at 310 nm, whose extinction coefficient decreased from an initial value of 180 to 70 l/mol.cm in 19 h at ambient (20°–28° C.) temperature. The maximum absorption initially observed eventually disappeared in three days. The $^1$H NMR spectrum of 2 in deuteriochloroform solvent showed four sharp singlets at $\delta$ 1.20, 1.33, 1.60, and 2.25 ppm (1:1:1:1) for the four CH$_3$ groups and two complex patterns in the 3.3–3.7 and 4.0–4.7 ppm regions for the four CH$_2$—O groups. The spectrum in deuterium oxide with 3-trimethylsilylpropanesulfonic acid sodium salt as an internal reference also showed four singlets in the CH$_3$ region at $\delta$ 1.17, 1.34, 1.60, and 2.21 ppm with relative intensities of 1:0.25:0.25:1 and two complex patterns in the 3.4–3.8 and 4.1–4.7 ppm regions; however, the spectrum became much more complicated quite soon within a few hours. The distillate gave the following infrared and combustion analysis: IR (neat): 3000–3350, 2950, 1735, 1635, 1460, 1370, 1245, 1125, 1060, 915, and 765 cm$^{-1}$; anal. calcd. for C$_{14}$H$_{22}$N$_2$O$_6$: C, 53.49; H, 7.05; N, 8.91; found: C, 52.76; H. 7.26; N, 8.69.

Photoreduction of 2 to DHM3

Oxazinone 2 (6.0 g, 0.019 mol) was dissolved in 500 ml of 2-propanol (Fisher). The solution was irradiated with a 450 W mercury immersion lamp through a Pyrex filter. Throughout the reacion the photochemical apparatus was immersed in a bath kept at 0° C. and nitrogen was bubbled through the solution. The disappearance of the oxazinone chromophore was monitored by UV spectroscopy. After 24 h, when the UV maximum at 323 nm had disappeared, the irradiation was stopped, and the solvent quickly rotary evaporated without delay at ambient temperature (20°–28° C.) first at 15–20 Torr, then at 1 Torr. The residue was dissolved in 70 ml of chloroform and the solution was stored in a freezer at about −18° C. for 6 days. The resulting pricipitate was collected by suction filtration, washed thoroughly with cold chloroform ($\approx 10°$ C.) and dried under vaccuum to give 2.9 g (48%) of a white powder, mp 121°–124° C. An additional crop of crystals (0.64 g) was obtained from the mother liquors after two more weeks in the freezer. Silica gel TLC eluting with dichloromethane-methanol (93:7, v/v) of both crops showed 3–4 spots with Rf 0.2–0.4, easily detected either with ninhydrin or phosphomolybdic acid, along with a very small spot, Rf 0.5, corresponding to the oxazinone 2. After recrystallization from acetonitrile, the product melting point (mp) was 145°–147° C., but TLC still showed more than one spot with Rf 0.2–0.4. The $^1$H NMR spectrum of DHM3 in DMSO-d$_6$ with CHD$_2$SOCD$_3$ as a reference at 2.49 ppm showed two CH$_3$ singlets as $\delta$ 0.93 and 1.31 ppm, an NH broad peak at 2.32 ppm, a CH$_2$OH multiplet at 3.3 ppm, a CH$_2$OCO singlet at 4.01 ppm, and an OH triplet at 4.92 ppm (J=5 Hz). Minor peaks in the spectrum were present in areas compatible with the presence of other stereoisomers. Infrared and analytical data are as follows: IR (KBr) 3160, 2900, 1715, 1455, 1285, 1220, 1040, 770, 715 cm$^{-1}$; anal. calcd. for C$_{14}$H$_{24}$N$_2$O$_6$: C, 53.15; H, 7.65; N, 8.85. Found: C, 53.00; H, 7.70; N, 8.84. A $1\times10^{-4}$M solution of DHM3 in water upon exposure to air at ambient temperature gave an absorption maximum at 310 nm (A=0.12 after 0.5 h). Upon exposure to air, a DMSO-d$_6$ solution of DHM3 gave an $^1$H NMR spectrum showing two methyl singlets at $\delta$ 1.07 and 2.09 ppm, a CH$_2$OH multiplet at 3.3 ppm and a CH$_2$OCO multiplet at 4.3 ppm, along with minor peaks in the 0.8–1.6 and 3.8–4.7 ppm regions. The same peaks were found as main features in the still more complex spectrum of oxazinone 2 in DMSO-d$_6$.

Kinetics of reaction of DHM3 with daunorubicin (6) in methanol solvent

Oxomorpholinyl dimer DHM3 (5.8 mg) was dissolved in 100 ml of oxygen-free dichloromethane by stirring under nitrogen for 1 h. A portion of the solution (1.0 ml, $1.8 \times 10^{-4}$ mmol) of DHM3 was transferred via syringe to the spectrophotometric compartment of a two-compartment Pyrex cell with attachment for connection to a vacuum line with an Ultra Torr Union. The solvent was then evaporated with a stream of nitrogen. Daunorubicin hydrochloride (8.83 mg) was dissolved in 100 ml of a methanolic solution of 18.9 mg of tris(hydroxymethyl)aminomethane (Tris) and 24.7 mg of Tris hydrochloride. A portion of this solution (2.5 ml, $3.9 \times 10^{-4}$ mmol of 6) was introduced via syringe into the second compartment of the cell. The methanol solution was freeze (liquid nitrogen)-pump ($2 \times 10^{-6}$ Torr)-thaw degassed through four cycles, sealed, and placed in a thermostatted cell holder at $25.1 \pm 0.1°$ C. for about 15 min. prior to mixing the solution with DHM3. After mixing, the average absorbance at 618 and 620 nm was recorded versus time. A non-linear least-squares treatment of the data as mentioned below gave a first order rate constant for bond homolysis of DHM3 equal to $1.8 \times 10^{-3}$ sec$^{-1}$. Silica gel TLC of the product solution eluting with dichloromethanemethanol (9:1, v/v) showed two spots with Rf=0 (unreacted daunomycin) and 0.7 (7-deoxydaunomycinone).

Kinetics of reaction of DHM3 with daunorubicin (6) in water solvent

A test similar to that described for the same reaction in methanol solvent (vide supra) was run. Oxomorpholinyl dimer DHM3 (1.38 mg, $4.37 \times 10^{-3}$ mmol) was dissolved in 0.5 ml of oxygen-free methanol and quickly transferred without delay into one compartment of the cell. The solvent was promptly removed under vacuum. Daunorubicin hydrochloride (11.9 mg) was dissolved in 100 ml of an aqueous solution of Tris (24.2 mg) and Tris hydrochloride (31.6 mg) and 2.6 ml of this solution ($4.18 \times 10^{-4}$ mmol of 6) was introduced into the other compartment of the cell. The sample was freeze-thaw degassed over three cycles as described above, sealed, and placed in a thermostatted cell holder at $10.0 \pm 0.1°$ C. for about 20 min prior to mixing. Full spectra between 320 and 800 nm were recorded every 10 sec for the first 125 sec, and then every 20 sec. From the absorbance change at 620 nm over the first 85 sec (50% reaction of daunorubicin), a non-linear least-squares treatment gave a first order rate constant for bond homolysis of DHM3 ($k_1$) equal to $6 \times 10^{-4}$ sec$^{-1}$ and a first order rate constant for destruction of 7 ($k_2$) equal to $2 \times 10^{-2}$ sec$^{-1}$. Treatment of the data obtained in the 164–225 sec interval gave $k_2 = 2.8 \times 10^{-2}$ sec$^{-1}$.

The results presented herein above and as shown in the schematic FIGS. 1 and 2 indicate that direct condensation of 2-amino-2-methyl-1,3-propanediol (1) with ethyl pyruvate in 1-butanol at reflux, followed by vacuum distillation, gives the 2,4-dimethyl-4-hydroxymethyl-1,3-oxazolidine-2-carboxylic acid ester of 5,6-dihydro-3,5-dimethyl-5-hydroxymethyl-1,4-oxazin-2-one (2). Evidence for the structure of the latter compound (2) is derived from elemental analysis, $^1$H NMR, IR and UV spectra, as well as chemical behavior. As described more specifically supra, the $^1$H NMR spectrum of 2 in deuteriochloroform showed four methyl singlets between 1.2 and 2.3 ppm, along with two very complex patterns between 3.3 and 4.7 ppm for the four —CH$_2$—O groups. The sharpness of the four methyl singlets suggests that 2 is mostly one of four possible diastereoisomers. The IR spectrum showed the bands characteristic of OH and/or NH stretching at 3000–3500, a very strong band at 1735 (C=O) and a band at 1635 cm$^{-1}$ (C=N). The UV spectrum of 2 in 2-propanol solvent showed a maximum at 323 nm, characteristic of the oxazinone ring.

In protic solvents, 2 slowly underwent equilibration with its "monomeric" form 5,6-dihydro-3,5-dimethyl-5-hydroxymethyl-1,4-oxazin-2-one (3), a compound analogous to the normal condensation products obtained from the reaction of ethyl pyruvate with a variety of 1,2-aminoalcohols. Indeed the absorbance of the UV maximum at 323 nm shown by a fresh solution of 2 in 2-propanol increased with time reaching a maximum extinction coefficient $\epsilon$ of 188 l/mole.cm from an original value of 157 l/mole.cm in about 20 hrs. 5,6-Dihydro-3,5,5-trialkyl-1,4-oxazin-2-ones show an $\epsilon$ value of 120–130 l/mole.cm at about 320 nm in alcohol solvents.

More extensive changes of $2 \rightleftharpoons 3$ into products deprived of the O=C—C=N chromophore appear to occur in water solvent. In fact the maximum at 310 nm ($\epsilon = 180$ l/mole.cm) of a water solution of 2 completely disappeared in a few days. $^1$H NMR spectra of 2 in D$_2$O also showed extensive changes occurring within a few hours.

UV irradiation of a solution of 2 in 2-propanol solvent produces the title compound DHM3 in more than 50% yield in about 20 hrs., a reaction which presents further evidence of the conversion of 2 into two mole equivalents of 3. UV and IR absorption at 323 nm and 1635 cm$^{-1}$, respectively, characteristic of the conjugated carbon-nitrogen double bond of 2, were absent in DHM3. Theoretically, DHM3 can exist in six different diastereoisomeric forms (two meso and four dl pairs). Actually the reaction mixture, which gave a correct elemental analysis, showed at least four distinct spots on TLC, even after recrystallization from acetonitrile. The $^1$H NMR spectrum of DHM3 in DMSO-d$_6$ solvent suggests that probably one stereoisomer heavily predominates over the other stereoisomers. Relatively strong peaks with the expected chemical shifts and areas appear as sharp signals accounting for most of the total spectrum, as described more particularly, vide supra.

The EPR spectrum of DHM3 in methanol solvent, at temperatures above 20° C., shows a 24 line pattern characteristic of the trialkyl-2-oxomorphlin-3-yl radicals from bond homolysis of bi(3,5,5-trialkyl-2-oxomorpholin-3-yl)s. At 50° C. the g-value of the radical was 2.0043 and the EPR splitting constants were $a_H{}^{CH3} = 10.2$ G, $a_N = 6.4$ G, and $a_H{}^{NH} = 5.3$ G. Oxidation of DHM3 by molecular oxygen back to oxazinone $2 \rightleftharpoons 3$ is indicated by the appearance of the peaks characteristic of the oxazinone ring in the $^1$H NMR spectrum of a oxygenated solution of DHM3. A solution of DHM3 in water, whose UV spectrum is featureless at $\lambda > 220$ nm, upon exposure to air quickly gives rise to an absorption maximum at 310 nm, characteristic of the oxazinone.

Reaction of DHM3 with daunorubicin 6

The oxomorpholinyl dimer DHM3 causes reductive elimination of the sugar moiety, daunosamine, of daunorubicin (6) in much the same way as the structurally related bi(3,5,5-trimethyl-2-oxomorpholin-3-yl) (9). (See Schematic FIG. 2). The reaction of DHM3 with 6 in a 1:2 molar ratio in oxygen degassed methanol at 25° C. gives 7-deoxydaunorubicinone 8 as the only reaction product via the tautomeric quinone methide intermediate 7. Monitoring the change of the absorbance with time in the 618–620 nm region, where only 7 shows a strong absorption, indicated that the formation and destruction of 7 follows consecutive first-order kinetics, first order in DHM3 and 7, suggesting a mechanism identical to that found for the reaction of 9 with 6. The kinetics were established by regressional, non-linear least squares fitting of the absorbance versus time data to equation 1, $$A_t = (\epsilon_7 k_1 [\text{DHM 3}]_o/(k_2-k_1))(e^{-k_1 t}-e^{-k_2 t})$$

where $A_t$ is the absorbance of 7 at time t, $\epsilon_7$ is the extinction coefficient of 7 at 618-620 nm, $[\text{DHM3}]_o$ is the concentration of DHM-3 at time zero, $k_1$ is the rate constant for bond homolysis of DHM3 and $k_2$ is the rate constant for tautomerization of 7 to 8. The value obtained for $k_1$, $1.8 \times 10^{-3}$ sec$^{-1}$, was approximately half that obtained for bond homolysis of 9. The values for $k_2$ ($1.3 \times 10^{-2}$ sec$^{-1}$) and $\epsilon_7$ (9,400±400 l/mol.cm) used in the calculation of $k_1$ were taken from the reports of the reaction of 9 with 6 (Kleyer, et al., *J. Am. Chem. Soc.* 1983, 105:2504; Kleyer, et al., *J. Am. Chem. Soc.* 1984, 106:2380).

The same reaction of DHM3 with daunorubicin (6) occurs in water solvent at comparable rate. Thus, when a ten-fold excess of DHM3 is reacted with an oxygen-free $2 \times 10^{-4}$M solution of 6 in buffered water (pH8) at 10° C., the absorbance of the solution at 618–620 nm, due to the tautomer 7, reaches its maximum after 125 sec and then decreases quickly, with an 80% decrease in 100 sec. Here again the formation and destruction of 7, as calculated from the data obtained in the first 85 sec of reaction, follows consecutive first order kinetics, first order in DHM3 and 7, with $k_1 = 6 \times 10^{-4}$ sec$^{-1}$, $k_2 = 2 \times 10^{-2}$ sec$^{-1}$ and $\epsilon_7 = 9600$. Calculation of $k_2$ from the absorbance data taken after 165 sec of reaction time, when only first order destruction of 7 is observed, gives a value of $2.8 \times 10^{-2}$ sec$^{-1}$. Possible slight error in data for the second measurement of $k_2$ probably results from light scattering due to precipitation of the sparingly soluble product, 7-deoxydaunorubicinone (8).

These kinetic measurements indicate that oxomorpholinyl dimer DHM3 has approximately the same reactivity with daunorubicin in water solvent as does oxomorpholinyl dimer 9 (TM-3) in methanol solvent. Thus, in water solvent DHM3 acts as a potent reducing agent for anthracycline compounds including quinone-anthracycline anti-tumor drugs such as aclarubicin, doxorubicin, 4-demethoxydaunorubicin and the like. It is postulated that DHM3 acts as a reducing agent for mitomycin C as well.

TABLE 1

| Kinetic measurements of TM3 reactivity with anthracycline compounds at 25° C. in methanol solvent. | |
|---|---|
| ANALOG | RATE CONSTANT $k_2$ (sec$^{-1}$) |
| DOXORUBICIN | $1.1 \times 10^{-2}$ |
| DAUNORUBICIN | $1.3 \times 10^{-2}$ |
| 4-DEMETHOXYDAUNORUBICIN | $9.0 \times 10^{-3}$ |
| MENOGARIL | $2.5 \times 10^{-3}$ |
| ACLARUBICIN | $9.0 \times 10^{-4}$ |

DHM3 as a rescue agent against extravasation injury

In order to produce anthracycline induced tissue damage, clinical grade doxorubicin (DOX) hydrochloride was obtained as a representative anthracycline chemical from the Drug Synthesis Branch, Developmental Therapeutics Program, National Cancer Institute. Each vial contained 10 mg DOX hydrochloride and 50 mg lactose which was reconstituted with 5.0 ml sterile 0.9% NaCl solution to give a final drug concentration of 2.0 mg/ml. DHM3 solution was prepared by dissolving 10 mg in ice-cold water which had been purged with $N_2$ gas for 5 minutes. Dissolution was facilitated by brief sonication to give a final concentration of 10 mg/ml. The solution was kept cold ($\approx$4° C.) and protected from air and light.

Animals

Female weanling miniature white swine weighing approximately 12 kg were obtained from the Veterinary Resources Branch, National Institutes of Health. The development of this strain of swine has been described previously (Sachs, et al., *Transplantation* 22:559–567, 1976). Each animal was housed in a 6×4 ft metabolic cage and was fed standard NIH show chow, 1.5 lbs twice daily.

Anesthesia

Each animal was anesthesized by intramuscular injections of ketamine, 20 mg/kg, xylazine, 20 mg/kg, and atropine, 1.0 mg. Following endotracheal intubation anesthesia was maintained with a mixture of nitrous oxide, halothane, and oxygen gas.

Drug Administration and Lesion Measurement

DOX HCl (2.0 mg/ml) was administered intradermally (i.d.) with a 25 gauge needle inserted approximately 4 to 5 mm into the skin. Following the injection of 0.5, 0.75 or 1.0 ml (1.0, 1.5, or 2.0 mg, respectively) DOX solution, the syringe was removed from the hub leaving the needle in place. After the indicated time interval, 1.0 ml (10 mg) DHM3 was injected through the same needle and the needle was then removed. Control sites received 1.0 ml sterile water instead of DHM3. The injection sites were along the mid-lateral aspect of each side of the swine and were 4–5 cm apart (6–8 injection sites per side). One animal was used for a dose experiment where DOX, 0.5 ml/site was injected along one side and 1.0 ml/site was injected along the contralateral side. Fifteen minutes later, DHM3 or water was injected into alternating sites as described above. A second animal received DOX, 0.75 ml/site along both sides. DHM3 or water was injected into alternating sites at times varying from 5 to 120 minutes following DOX administration.

In a separate study, equimolar amounts of several compounds used in experimental or clinical cancer chemotherapy were injected into pig skin using the same method described above. Paired injection sites were treated 15 minutes later with either $H_2O$ or DHM3 in duplicate.

All lesions were measured by a single observer with metric calipers three times weekly for two weeks, followed by weekly measurements thereafter. The areas of skin ulceration and induration were estimated by the product of the cross perpendicular diameters. The total toxicity of DOX-induced skin ulceration was determined by calculating the area under the ulceration-time curve (AUC) in mm$^2$-days. Each swine was observed for 8 weeks.

In order to assess the extent of tissue injury following intradermal DOX or DHM3, incisional biopsies were performed on representative lesions 6 and 20 days following drug injection. These samples were placed in 10% buffered formalin and processed for examination by standard light microscopy (Pathco Inc., Potomac, MD.).

Results

Figure 3:
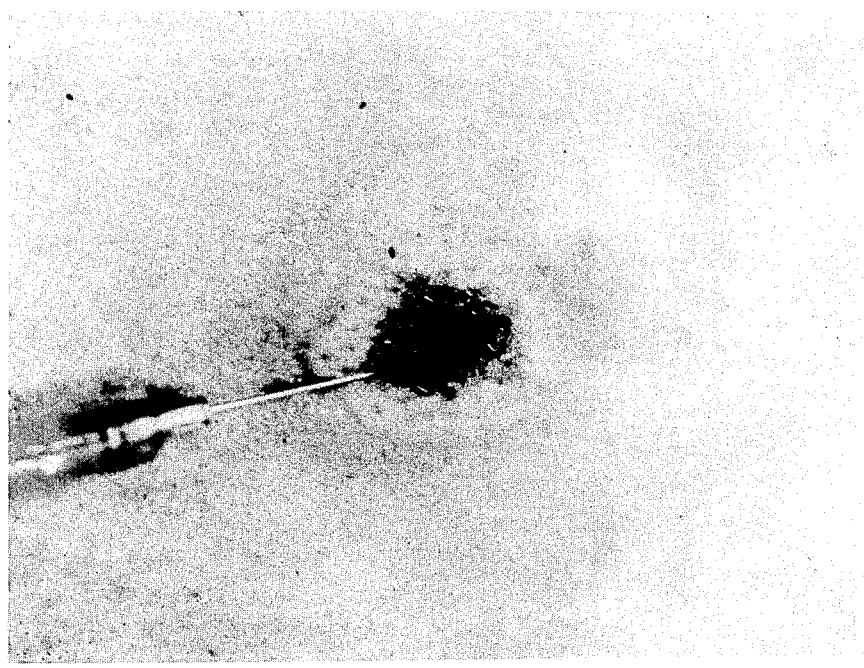
FIG. 3 shows the bullae formed following the intradermal injection of DOX, 2.0 mg into swine skin. The central dark area is red-orange staining of the epidermis by drug.

Following the initial injection of DOX, there was a raised bleb with a central red-orange staining of the skin (FIG. 3). If water were injected into the same site, the bleb enlarged and the stain became lighter orange in color. However, if DHM3 were injected, the color immediately changed to a rusty brown. Thirty minutes after the completion of all injections the raised blebs each measured approximately 15 mm in diameter and no distinction with regard to color of the stained skin (dark red-orange) could be discerned between sites.

Figure 4:
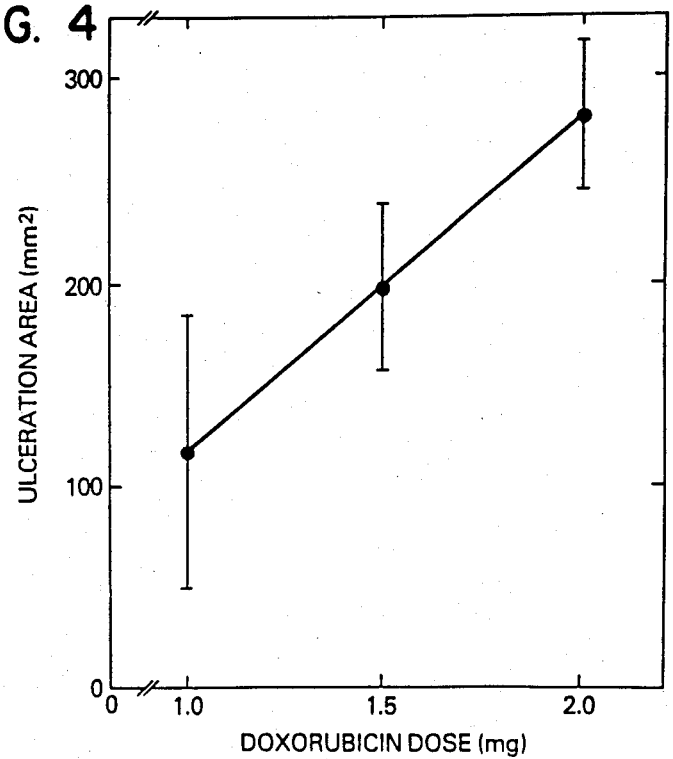
FIG. 4 shows the relationship of the maximal ulcer size as measured by the cross product of perpendicular diameters to DOX dose (mg) administered i.d. Each point represents the mean±S.D. of triplicate experiments.
Figure 5:
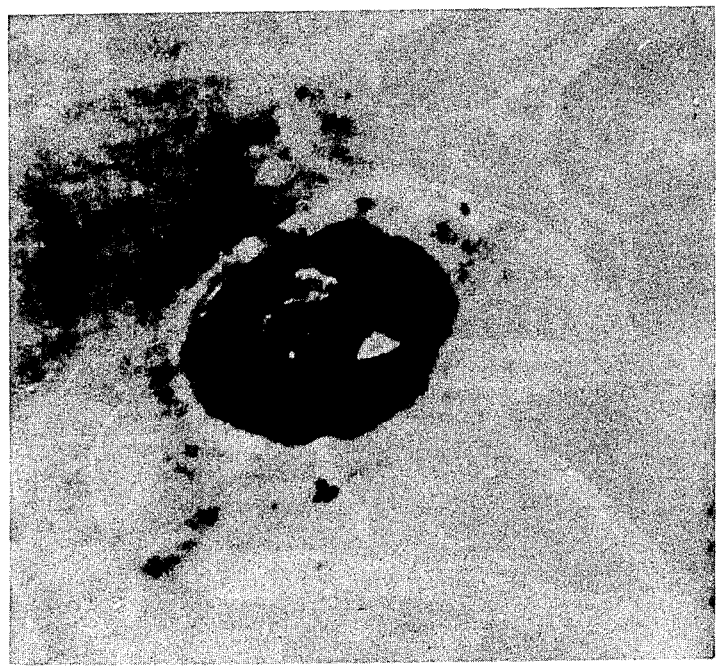
FIG. 5 shows a typical skin lesion 21 days following the injection of DOX, 2.0 mg i.d. The ulcer crater is covered by a full thickness dark eschar measuring 14×19 mm. There is a circumferential irregular area of erythema and induration measuring 26×32 mm.

DOX produced a predictable and reproducible skin ulceration the size of which was linearly dependent on the dose (volume) of DOX administered in the range of 0.5 to 1.0 ml (FIG. 4). Ulcer formation began 7-8 days following DOX administration. The ulcer crater usually contained a dark, central full thickness eschar surrounded by an erythematous, firm induration (FIG. 5). The ulcer reached maximal size at 3 weeks following DOX, and was completely healed by 7 weeks.

Figure 6:
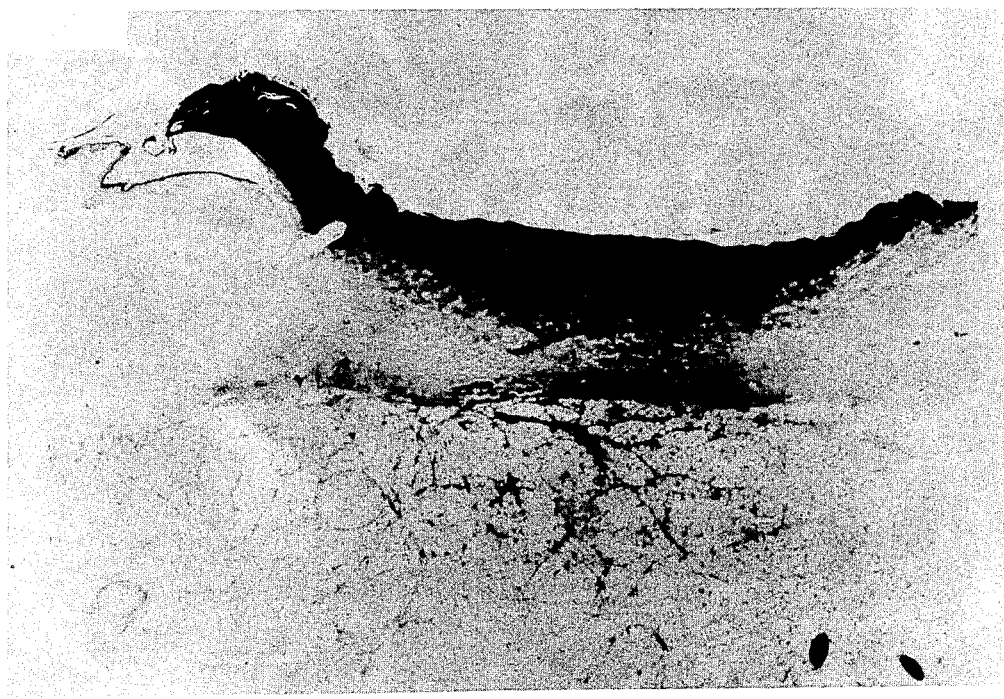
FIG. 6 shows the light microscopic appearance of a skin lesion 21 days following DOX, 2.0 mg i.d.

Microscopic examination of skin biopsy specimens were reviewed independently by two pathologists. The lesions caused by DOX injection showed extensive coagulation-type necrosis of epidermis, dermis, and subcutaneous tissue, including muscle. There was epithelial hyperplasia as well as a moderate dermal chronic multifocal inflammation at the periphery of the necrotic area (FIG. 6).

Figure 7:
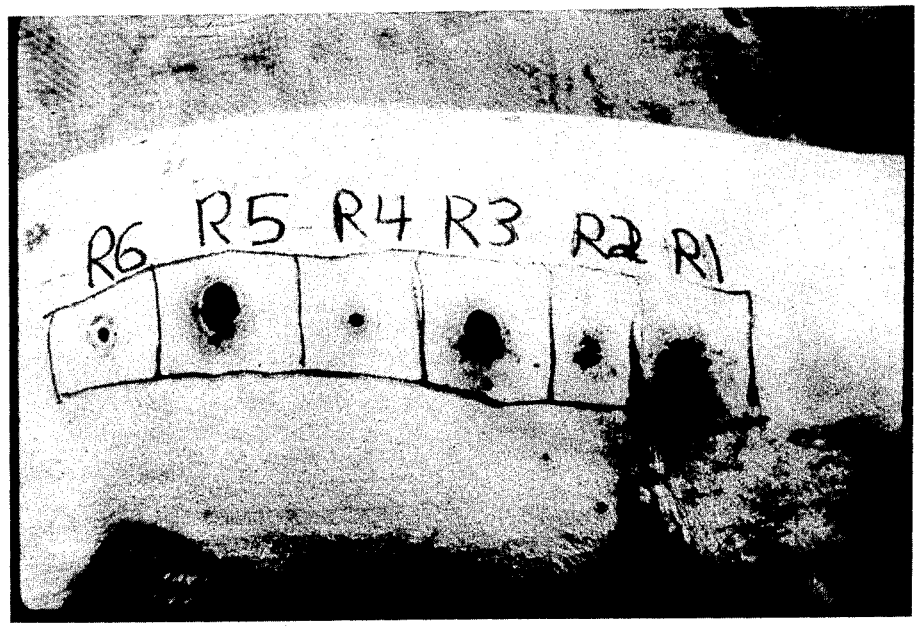
FIG. 7 shows skin lesions 21 days following DOX with and without DHM3 protection. On day 1 each site received DOX, 2.0 mg i.d. Fifteen minutes later sites R1, R3, and R5 received sterile $H_2O$, 1.0 ml and sites R2, R4, and R6 received DHM3 10.0 mg in 1.0 ml sterile $H_2O$ through the same needle.
Figure 8:
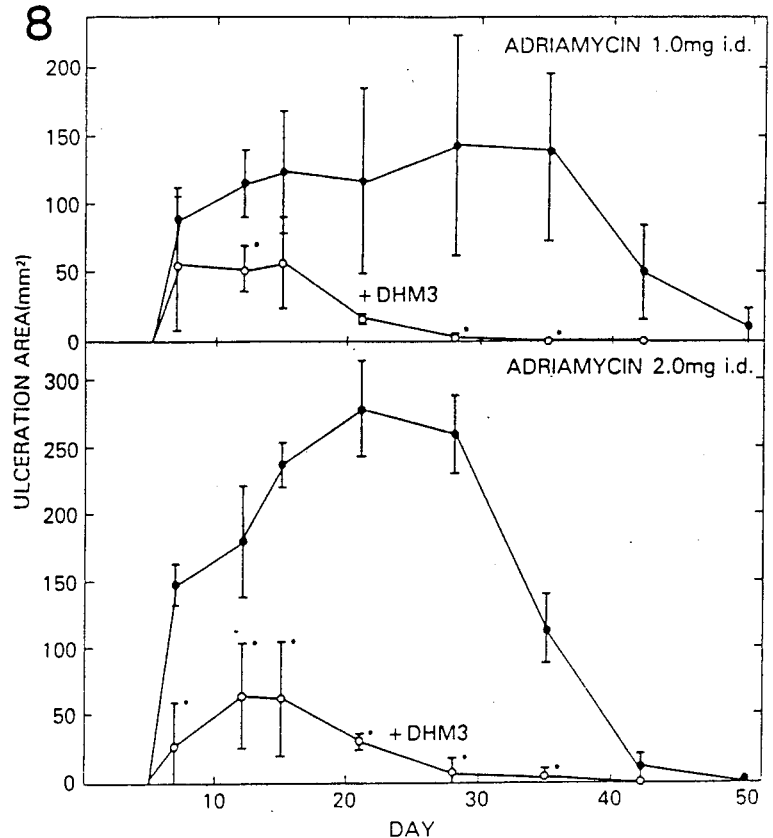
FIG. 8 shows the time course of DOX induced skin ulcer control (•) and treated with DMH3 (o) as described. The ulceration area is estimated by the cross product of the perpendicular diameters of each lesion. Each point represents the mean±S.D. of triplicate experiments. (*) Indicates $p<0.05$, determined by two-tailed t-test for independent means.
Figure 9:
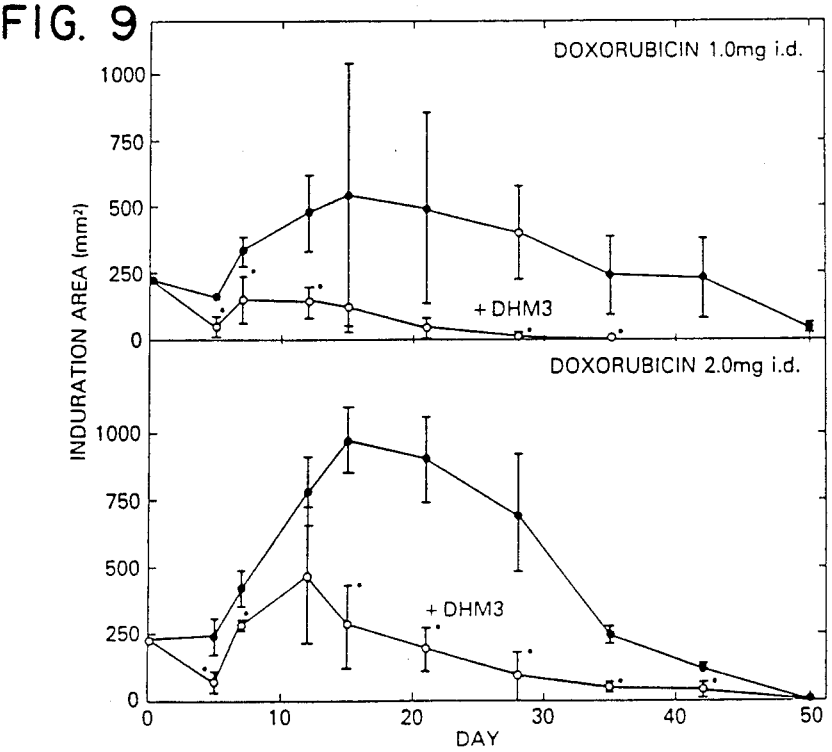
FIG. 9 shows the time course of DOX induced skin induration control (•) and treated with DHM3 (o) as described. The induration area is estimated by the cross product of the perpendicular diameters of each lesion. Each point represents the mean±S.D. of triplicate experiments. (*) Indicates $p<0.05$, determined by two-tailed t-test for independent means.

If 1.0 ml (10 mg) DHM3 was injected into the same site 15 minutes after 1.0 ml (2.0 mg) DOX, the extent of skin necrosis was greatly reduced (Table 2, FIGS. 7 and 8). Peak area size of the ulcer was reduced 80%, and healing was complete within 5 weeks for DHM3 treated sites compared to 7 weeks for control. DHM3 reduction of DOX induced injury following 0.5 ml (1.0 mg) DOX was similar (Table 2, FIG. 8). The reduction of the size of surrounding induration was observed to parallel the ulcer measurements (FIG. 9).

Figure 12:
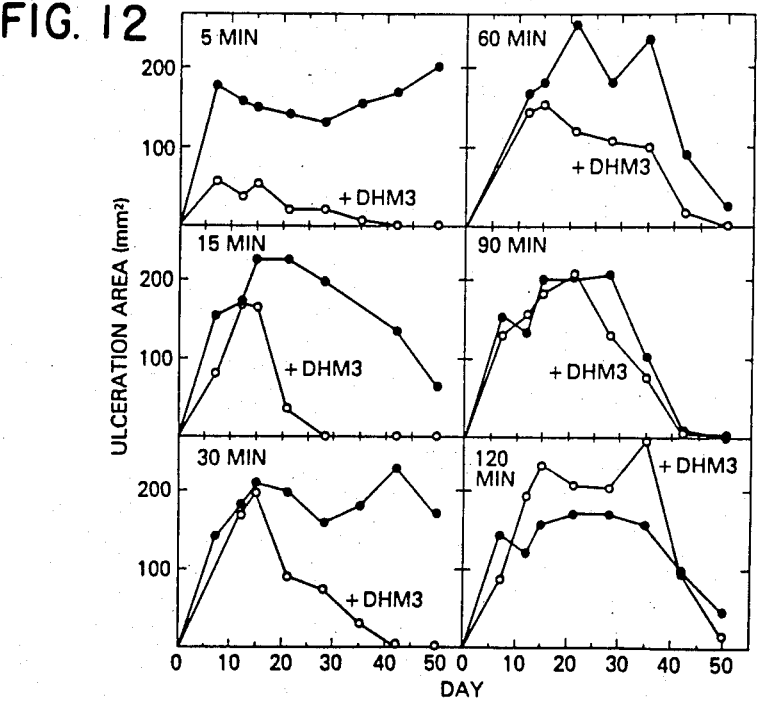
FIG. 12 shows the time course of DOX-induced skin ulceration when sterile water (●) or DHM3 (o) is injected at varying time intervals following DOX 1.5 mg i.d. as described in Materials and Methods. The ulceration area is estimated by the cross product of the perpendicular diameters of each lesion. Each point represents a single experiment.
Figure 10:
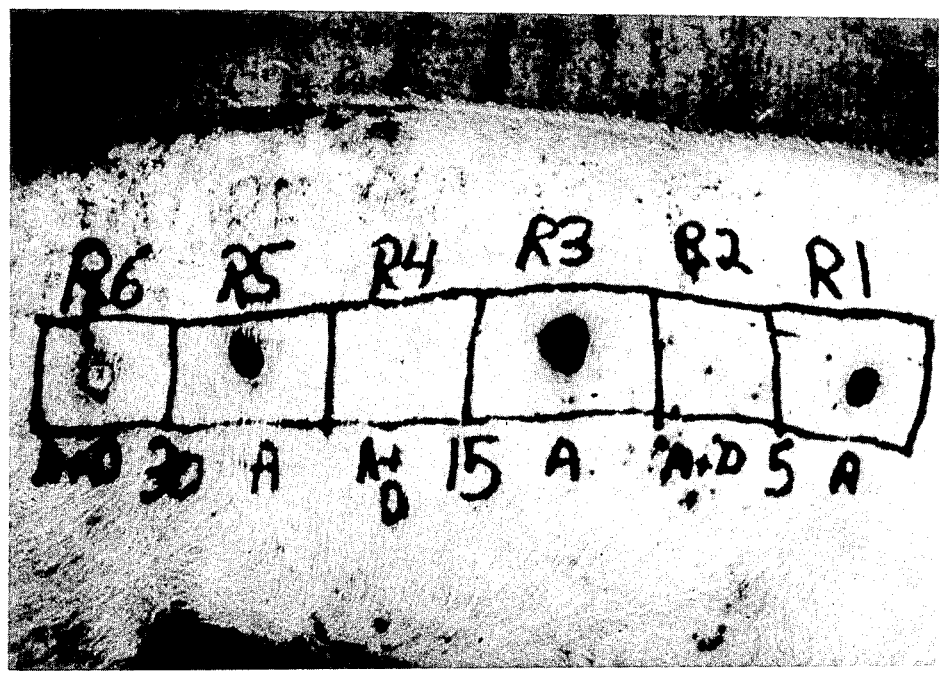
FIGS. 10 and 11 show skin lesions 21 days following DOX with and without DMH3 protection. On day 1 each site received DOX 1.5 mg i.d. At varying time intervals (indicated, in minutes) each odd numbered site received sterile $H_2O$ 1.0 ml and each even numbered site received DHM3 10.0 mg in 1.0 ml sterile $H_2O$ through the same needle.
Figure 11:
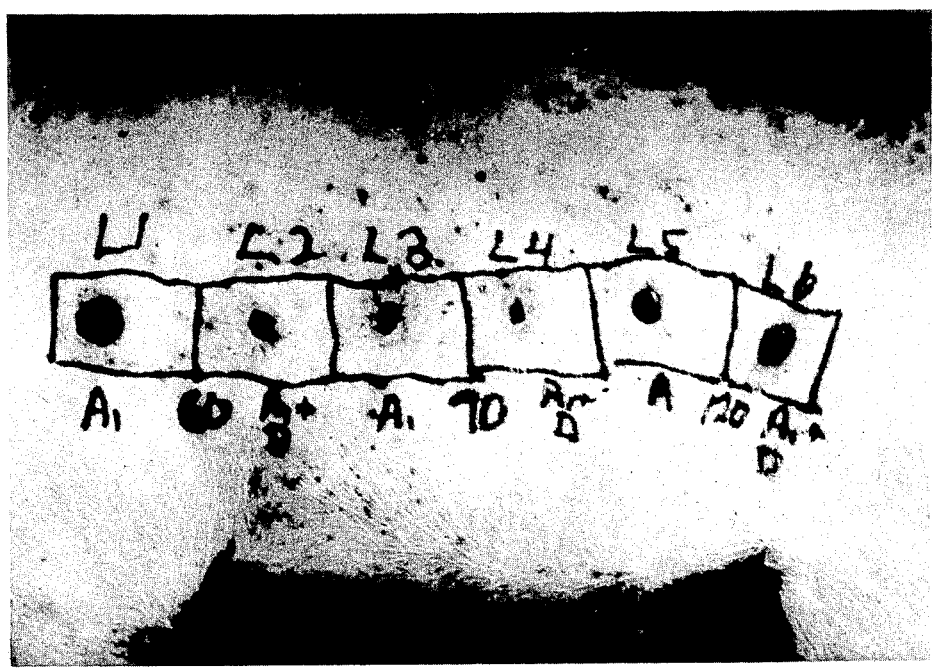

Timing the administration of DHM3 after DOX has a profound effect on the protection process (Table 2, FIGS. 10-12). Optimal protection was achieved when DHM3 was injected 5 min after DOX. Progressively less protection occurred as the interval between DOX and DHM3 injections increased to 60 min. If the interval were greater than 60 min, DHM3 administration offered no protection against DOX injury. Control i.d. DHM3 injections were well tolerated by the test animals and no ulcer formation occurred as was the case with water alone.

Biopsy sites that received DOX followed by DHM3 15 minutes later showed histological changes similar to DOX alone except for a reduced extent of necrosis. DHM3 injection alone did not cause any tissue injury except for mild upper dermis congestion.

Several anthracycline analogs and mitomycin C caused tissue necrosis to a varying degree and DHM3 was effective in all cases. In contrast, DHM3 did not protect against vinca alkaloid nor mitoxantrone-induced skin injury (Table 3).

TABLE 2

The effect of DHM3 treatment on the total toxicity of skin ulceration caused by three doses of DOX, i.d.

| Treatment | Interval[a] (min) | AUC (mm² · days) DOX 1.0 mg | DOX 1.5 mg | DOX 2.0 mg |
|---|---|---|---|---|
| H₂O (Control) | 15 | 4740 ± 180[b] | 9540 | 7680 ± 300[b] |
| DHM3 10 mg | 5-120 | | 7440 ± 1120[c] | |
| | 5 | | 960 | |
| | 15 | 840 ± 420[b] (p < .005) | 2220 | 1020 ± 420[b] (p < .001) |
| | 30 | | 3240 | |
| | 60 | | 4020 | |
| | 90 | | 5340 | |
| | 120 | | 8400 | |

[a]Time interval between DOX and either H₂O or DHM3 injection as described.
[b]Mean of 3 lesions. P value determined by two-tailed t-test for independent means of DHM3 treatment compared to control for each dose of DOX.
[c]Mean of 5 lesions.

TABLE 3

Protection Against Drug-Induced Skin Necrosis in the Swine Model by DHM3

| | | Percent Reduction of Maximal Ulcer Size |
|---|---|---|
| Drugs for which protection observed | | |
| Exper. 1: | Adriamycin | 77% |
| Exper. 2: | Adriamycin | 40% |
| | Daunorubicin | 39% |
| Exper. 3: | Mitomycin C | 58% |
| | 5-Iminodaunorubicin | 53% |
| Exper. 4: | 4-Demethoxydaunorubicin | 79% |
| | Menogaril | 61% |
| | Aclarubicin | 46% |
| | 4'-Epidoxorubicin | 51% |
| Drugs for which no protection observed | | |
| | Vincristine | |
| | Vinblastine | |
| | Mitoxantrone | |

The above results indicate that the intradermal injection of DOX in swine produces predictable and reproducible dose-dependent skin necrosis. The natural history, gross appearance and histologic features of the lesions closely resemble that observed in humans following inadvertent extravasation of DOX (Rudolph, et al., Cancer 38:1087-1094, 1976; Reilly, et al., Cancer 40:2053-2056, 1977). The present tests demonstrate the reliability of the swine model for studying human extravasation injury resulting from anthracycline or other compounds. The results here are similar to those of Okano, et al., Cancer Treat. Rep. 67:1075-1078, 1983; however, they report a smaller and more variable ulcer following DOX, 2 mg/site i.d.

The injection of DHM3 into the same site up to 60 min after i.d. DOX, provides considerable protection from skin necrosis as measured by maximal ulcer area and time required for healing. If DHM3 were administered after about an hour of DOX, then no protection is observed.

The mechanism of anthracycline induced skin necrosis is poorly understood. However, several hypotheses have been proposed (Cox, Am. J. Hosp. Pharm. 41:2410-2414, 1984). The anthracyclines are known to have a high affinity for cellular DNA, and they are thought to intercalate between nucleic acid base pairs resulting in inhibition of DNA and RNA synthesis. This leads to cell death and, in the case of skin injury, the anthracyclines may be released from dying cells to be taken up by nearby cells where the cycle repeats itself. This mechanism has been proposed to account for the persistance of drug in tissue (as determined by microscopy) and for the indolent and progressive nature of tissue damage (Luedke, et al., *Plast. Reconstr. Surg.* 63:463–465, 1979). Alternatively, the anthracyclines and mitomycin C are capable of undergoing enzymatic electron reduction to form either primary or secondary free radical species which may cause cell death by damage to vital macromolecules, including DNA and membrane lipids (Bachur, et al., *Mol. Pharmacol.* 13:901–910, 1977).

Based on these postulated mechanisms of action, a number of potential treatments and antidotes have been proposed for anthracycline and mitomycin C extravasation. Thus, the application of cold may retard drug diffusion throughout the tissue, prevent drug uptake into cells, lower cellular metabolic rates, and slow the localized inflammatory response. The use of sodium bicarbonate has been proposed to alter local pH and thereby decrease cellular uptake and binding of the anthracyclines to DNA. Free radical scavengers such as dimethyl sulfoxide and alpha-tocopherol have been purported to reduce the size of ulceration in some animal models but not in all. Additionally, there are anecdotal reports of dimethyl sulfoxide treatment for DOX extravasation in patients. Corticosteroids, $\beta$-adrenergic agents, and antiinflammatory drugs have also been suggested to be effective in animals or patients to reduce skin injury from anthracyclines. All of these putative treatments are based on an incomplete understanding of the mechanism of this drug-induced injury. Furthermore, no one antidote has been shown consistently to protect significantly against extravasation necrosis.

The substituted 2-oxomorpholin-3-yl radical dimers of the present invention react rapidly, irreversibly, and quantitatively with DOX in vitro to form the pharmacologically inactive 7-deoxydoxorubicin aglycone. It is postulated that these radical dimers undergo bond homolysis to the DHM3 radical which then reductively cleaves DOX as shown in FIG. 2.

The immediate color change observed in the skin following DHM3 injection and the significant reduction in skin necrosis as demonstrated herein suggest that the same DHM3-DOX reaction described in vitro most likely occurs in situ to inactivate the parent drug. The time dependency of DHM3 protection suggests that most of the DOX is bound to tissue sites after 60 minutes and therefore, unavailable to react with DHM3. These results corroborate those obtained in mice where DOX toxicity may be prevented by the systemic administration of the radical dimer (Banks, et al., *Cancer Chemother. Pharmacol.* 11:91–93, 1983; Averbuch, et al., *Proc. Am. Soc. Clin. Oncol.*, 1985); Averbuch, et al., *Cancer Res.*, in press December 1985).

In summary, the results presented herein and the known anatomical similarities between pig and human skin (Montagna, et al., *J. Invest. Derm.* 43:11–21, 1964; Bartek, et al., *Invest. Derm.* 58:114–123, 1972) establish the efficacy of radical dimers such as DHM3 as effective antidotes for anthracycline- and mitomycin C-induced extravasation necrosis.

Of course, DHM3 of the present invention can be administered in any pharmaceutically acceptable form, for example an injectable composition in a sterile, non-toxic carrier (e.g. physiological saline), a topical paste, gel, powdery preparation, micro-capsule, an emulsion and the like.

It is understood that the examples and embodiments described herein are for illustrative purposes only and that various modifications or changes in light thereof will be suggested to persons skilled in the art and are to be included within the spirit and purview of this application and the scope of the appended claims.

We claim:

1. Bi(3,5-dimethyl-5-hydroxymethyl-2-oxiomorpholin-3-yl) compound.

2. A method of protecting mammals against anthracycline or mitomycin C induced tissue damage comprising administering to said mammals a protective amount of bi(3,5-dimethyl-5-hydroxymethyl-2-oxomorpholin-3-yl) in a pharmaceutically acceptable carrier.

* * * * *